(12) United States Patent
Chatham

(10) Patent No.: US 10,639,436 B2
(45) Date of Patent: May 5, 2020

(54) DEVICE FOR MANIPULATING RESPIRATORY AIR FLOW AND USE THEREOF

(76) Inventor: Kenneth Chatham, Usk (GB)

( * ) Notice: Subject to any disclaimer, the term of this patent is extended or adjusted under 35 U.S.C. 154(b) by 324 days.

(21) Appl. No.: 13/138,570

(22) PCT Filed: Mar. 4, 2010

(86) PCT No.: PCT/GB2010/050380
§ 371 (c)(1),
(2), (4) Date: Oct. 14, 2011

(87) PCT Pub. No.: WO2010/100499
PCT Pub. Date: Sep. 10, 2010

(65) Prior Publication Data
US 2012/0041329 A1    Feb. 16, 2012

(30) Foreign Application Priority Data
Mar. 4, 2009   (GB) .................................. 0903619.5

(51) Int. Cl.
*A61B 5/08* (2006.01)
*A61M 15/00* (2006.01)
*A63B 23/18* (2006.01)
*A61B 5/087* (2006.01)
*A61M 16/08* (2006.01)
*A61M 16/00* (2006.01)
*A63B 21/00* (2006.01)

(52) U.S. Cl.
CPC ......... *A61M 15/0086* (2013.01); *A61B 5/087* (2013.01); *A61M 15/0016* (2014.02); *A61M 16/0866* (2014.02); *A63B 23/18* (2013.01); *A61M 2016/0027* (2013.01); *A63B 21/00069* (2013.01); *A63B 2220/56* (2013.01)

(58) Field of Classification Search
CPC ........ A63B 21/00058; A63B 21/00069; A61B 5/087
USPC .................................................. 600/529–538
See application file for complete search history.

(56) References Cited

U.S. PATENT DOCUMENTS

| | | | | |
|---|---|---|---|---|
| 3,924,611 A | * | 12/1975 | Galitsky | ........................ 600/539 |
| 4,060,074 A | * | 11/1977 | Russo | .................. A61B 5/0875 |
| | | | | 128/200.18 |
| 4,534,343 A | * | 8/1985 | Nowacki | ........... A61M 15/0086 |
| | | | | 128/200.23 |
| 4,981,295 A | | 1/1991 | Belman | |

(Continued)

OTHER PUBLICATIONS

Larson, Inspiratory Muscle Training with a Pressure Threshold Breathing Device in Patients with Chronic Obstructive Pulmonary Disease, Am Rev Respir Dis, 1988; 138:689-696, USA.

(Continued)

*Primary Examiner* — Eric J Messersmith
(74) *Attorney, Agent, or Firm* — Owen J. Bates

(57) ABSTRACT

A device comprising a unit (1) through which a subject can breathe, the unit comprising: an opening (AA) to allow airflow communication to the outside of the device; a mouthpiece element (2) through which the subject can breathe air in from and out into the device; and means for providing resistance (4) to airflow positioned between the opening and the mouthpiece element, said means being arranged to controllably vary the resistance to airflow during inspiration or expiration. Also provided are methods for the use of such a device.

23 Claims, 4 Drawing Sheets

(56) References Cited

U.S. PATENT DOCUMENTS

| | | | |
|---|---|---|---|
| 5,655,520 A * | 8/1997 | Howe | A61M 15/0086 |
| | | | 128/203.12 |
| 6,585,662 B1 * | 7/2003 | Jones et al. | 600/538 |
| 6,631,716 B1 * | 10/2003 | Robinson | A61M 16/20 |
| | | | 128/204.21 |
| 6,679,250 B2 * | 1/2004 | Walker et al. | 128/200.21 |
| 6,708,688 B1 | 3/2004 | Rubin | |
| 6,718,969 B1 | 4/2004 | Rubin | |
| 8,459,255 B2 | 6/2013 | Spurling | |
| 2008/0053452 A1 * | 3/2008 | Brown et al. | 128/207.12 |

OTHER PUBLICATIONS

Hart, Evaluation of an inspiratory muscle trainer in healthy humans, Respiratory Medicine (2001) 95, 526-531.
International Preliminary Report on Patentability dated Sep. 6, 2011 in International PCT Application PCT/GB2010/050380 Applicant: Chatham.

* cited by examiner

DEVICE FOR MANIPULATING RESPIRATORY AIR FLOW AND USE THEREOF

FIELD OF THE INVENTION

The present invention relates to a device for manipulating respiratory air flow either into or out of the lungs and to methods for the use of such a device. In particular, the invention relates to a device for providing instantly variable resistance to airflow during inspiration or expiration which may be used for improving the delivery of inhaled drugs, augmenting airway clearance techniques and providing measurements of, and training for, the respiratory muscles.

BACKGROUND OF THE INVENTION

Airflow into the lungs is proportional to the negative pressure generated by the contraction of the inspiratory muscles (the diaphragm and chest wall muscles) and inversely related to the resistance within the airway. Airflow ceases when the distending negative pressure is less than the elastic recoil of the lungs themselves (equal pressure point) and the respiratory cycle begins again. The duration of inspiration is therefore positively related to pressure. The volume of air moved is finite and reflects individual vital capacity. Airflow ceases when total lung capacity is reached and no more air is available to achieve flow. At this point the inspiratory muscles are in their fully shortened position.

Control of air flow and the depth of breathing is known to be important in therapy. Treatment of patients with pulmonary disease, for example, commonly involves administration of drugs directly into the lungs and in addition to the particle size of the drug, inspiratory flow rate and breathing patterns are known to have an effect on determining the depth of penetration of the administered drug into the lungs. Airway clearance techniques for clearing sputum retained in the airways of the lungs arising, for example, from pulmonary inflammation or cystic fibrosis, also commonly rely on changes in the depth of inspiration and augmentation of shearing forces to facilitate movement of retained secretions from the periphery of the lung to the central airways where they can be expectorated. Respiratory muscle training methods involving the subject meeting a target airflow within progressively reduced time periods in order to strengthen and train the respiratory muscles are also well known.

A number of devices which can be used to modify air flow into or out of the lungs have been proposed. Examples include devices offering resistance to inspiration which may be used in inspiratory muscle training techniques such as the Powerbreathe and Threshold trainers (see, for example, Larson et. al., American Review of Respiratory Disease 138, 689-96 (1998), Hart et. al, Respiratory Medicine 536-531 (1995)). These require the user to breathe against a pre-set spring valve which requires a certain pressure to open it. Disadvantages associated with these devices are that they do not fix breathing frequency, provide little biofeedback and once the valve is open, they offer no further resistance. Resistive devices without a valve, such as the Pflex trainer (Chatham, British Journal of Therapy and Rehabilitation 2(1), 31-35 (1995)) are also known. These type of devices increase resistance by having subjects breathe through a progressively smaller hole but as flow, pressure and timing are not fixed, a training response is not ensured.

Other respiratory training devices known in the art include the RT2 and Trainair devices. In these devices resistance is applied by the use of a fixed 2 mm leak within the manometer used. They are capable of providing computerised biofeedback and have been used in through-range training, applying fixed load training with resistance applied from residual volume (breathing all the way out) to total lung capacity (breathing all the way in) in healthy subjects and patient groups. As the leak is fixed, however, this directly affects the nature of the training by altering and fixing the velocity at which the contracting inspiratory muscles shorten.

Software has been developed to assist in analysing breathing patterns and providing feedback when a subject is endeavouring to modify his breathing. For example, TIRE (Test of Incremental Respiratory Endurance) is a package that determines maximum inspiratory pressure (MIP), which is related to inspiratory muscle strength; sustained maximum inspiratory pressure (SMIP) which reflects single breath work capacity, and Σ SMIP as a measure of inspiratory muscle endurance.

One application in which manipulation of breathing patterns by the application of controlled resistance to airflow could be potentially be enormously beneficial is in improving the delivery of pharmaceuticals from a nebuliser to a target area in the lungs. A major difficulty associated with inhalation drug delivery is in achieving specific and targeted deposition of the inhaled drug deep into the lung. In practice, many of the drug particles are deposited in the facemask of the nebuliser, in the mouth or in the upper airways, leading to high levels of drug wastage (often in the region of 60 to 80%) and the possibility of side effects. Improving the efficacy of delivery into the deep lung would allow the more economical and clinically effective use of a wide range of commonly used drugs such as antibiotics, anti-inflammatories and beta-agonists, as well as costly specialised drugs that require pulmonary delivery, such as interleukin 1 receptors, alpha antitrypsin, pulmozyme, gene therapeutics and interferons.

To date, most efforts have concentrated on particle size reduction to enhance deeper penetration into the lungs. However it is known that improved inhalation technique can also play a vital role in maximising effective deposition. For example, breath holding has some effect in allowing deposition deeper in the lung but there is a need for further development to exploit the potential of breathing control in this area.

Airway clearance is another therapeutic area where breathing technique is known to be of great importance. For example effective sputum clearance is vital in managing conditions such as cystic fibrosis. There is currently no general agreement as to which technique is most effective. A common theme of interventions such as the active cycle of breathing techniques, autogenic drainage and PEP therapy is the use of breathing from different lung volumes and augmenting shearing forces to facilitate movement of retained secretions from the lung periphery to central airways where they can be expectorated.

Devices which apply resistance to inspiration at the mouth, such as the RT2 device, have been found to be beneficial in increasing peripheral clearance by extending inspiratory time and prolonging intra-airway pressure status, so overcoming elastic recoil and delaying the onset of the equal pressure point.

Inspiratory muscle training is another potentially valuable therapeutic strategy, which has been applied successfully in several disease states and in training elite athletes. A strength/endurance response has been seen with reductions in blood lactate (an indicator of aerobic capacity). Again, however, the potential of the approach remains to be fully realised.

There therefore remains a continuing need for the development of improved devices for manipulating respiratory air flow, in particular for use in methods for providing targeted pulmonary drug deposition, airway clearance and respiratory muscle training.

SUMMARY OF THE INVENTION

The present invention is based on the finding that varying the resistance to airflow instantly during the course of the breathing cycle provides an effective means for manipulating respiratory air flow, thereby facilitating targeting of inhaled drugs, effective respiratory muscle training for different outcomes, strength, endurance or power and by recruiting different muscle fibre types and refinement of airway clearance techniques.

The invention therefore provides, in a first aspect, a device comprising a unit through which a subject can breathe, the unit comprising:

an opening to allow airflow communication to the outside of the device;

a mouthpiece element through which the subject can breathe air in from and out into the device; and means for providing resistance to airflow positioned between the opening and the mouthpiece element, said means being arranged to controllably vary the resistance to airflow during inspiration or expiration.

Also provided according to further aspects of the invention are methods for the use of such a device.

By means of the invention, resistance to airflow into or out of the lungs may be varied during the course of the breathing cycle, thereby affording improved control over the depth and targeting of drug deposition of inhaled drugs by allowing various lung areas, including the lung periphery, to be specifically targeted for maximal deposition, for example, and also affording increased effectiveness of inspiratory muscle training techniques. The ability to provide variable resistance during both inspiration and expiration may also be used to advantage to refine established airway clearance techniques in an accurate manner, with variable resistance during inspiration allowing penetration of airflow to variable lung volume and variable resistance during expiration providing back pressure (positive expiratory pressure or PEP) to prevent premature airways collapse.

By operating the device according to the invention in conjunction with a system to provide feedback relating, for example, to the flow or air, the air pressure and the duration of inspiration or expiration, it is possible to optimise the timing and extent of variation of the resistance depending on the intended application and the individual subject. In this way, it is possible, for example, to ensure that an inhaled drug is deposited at that part of the respiratory system most appropriate to its mode of action or to refine airway clearance techniques and respiratory muscle training methods to improve their efficacy. Biofeedback will ensure adequate loads and patient interaction.

Nebuliser devices having variable resistance orifices to provide a variable resistance to airflow have been described previously, see, for example, U.S. Pat. No. 6,631,721 B, but in such devices the resistance is varied prior to inhalation or expiration and not during inhalation or expiration as in the present invention. Manipulating the resistance to airflow to reduce the resistance during the inspiratory or expiratory effort (thereby causing the pressure to drop such that any drugs in suspension in the airway will lose their forward momentum and become deposited in the lung) allows the delivery of inhaled drugs to be controlled by targeting drug deposition to any desired lung area or volume and this represents a significant advantage for the method of the present invention compared to drug deposition methods known in the art.

Manipulating the resistance to airflow during the course of the breathing cycle has also been found to be beneficial in augmenting known airway clearance techniques. In order to clear sputum from the lungs, known airway clearance techniques rely on prolonged inspiration (to move air behind the sputum plugs) combined with variable resistance to expiration in order to provide a positive expiratory pressure (PEP) to splint the airway and so prevent airways collapse as the airflow accelerates and moves secretions towards the mouth prior to expectoration. The PEP has to be adjusted to the individual patient and in the techniques known to date this has involved breathing against a pre-set spring valve or breathing through progressively smaller holes. Varying the resistance during the inspiratory cycle according to the present invention allows more sophisticated training strategies to be implemented. For example, different muscle fibres can be trained by increasing or decreasing the velocity at which shortening occurs.

DETAILED DESCRIPTION OF THE INVENTION

The unit through which the subject can breathe in the device according to the invention may be of any convenient size and shape conventionally used in inhalation or expiration devices, the means for providing resistance to airflow and arranged to controllably vary resistance during inspiration or expiration being positioned therein. Conveniently, the unit comprises a tubular passageway within which are positioned the means for providing resistance to airflow, which tubular passageway is preferably cylindrical and which may conveniently be made from any suitable air-tight material conventionally used in the art such as durable or moldable plastics materials.

The unit is preferably associated in fluid communication with a hollow mouthpiece element at one end of the unit for insertion into the subject's mouth, the mouthpiece element conveniently being mouth-shaped. Additionally, the unit may incorporate an air filter. The end of the unit distal to the mouthpiece end is provided with an opening to allow airflow communication to the outside of the device, allowing air to enter into the device and exhaled gases to be expelled from the device. This opening may be reversibly sealable, by sealing means such as a flap valve, thereby, for example, allowing inspiratory airflow but closing to allow measurement of PEP.

The end of the unit distal to the mouthpiece end is preferably connected to a pressure sensing device which provides a means for determining the pressure achieved and the positive expiratory pressure (PEP). For those applications where variation of resistance during inspiration is required, the pressure sensing device is instead conveniently positioned proximally between the mouthpiece element and the means for providing resistance to the airflow as this provides the measure of inspiratory pressure, flow and time from which the algorithms of lung volume and estimates of training loads are derived.

Where the unit is intended to be used as a stand alone unit without using a computer to provide detailed feedback, a simple manometer may conveniently be used to measure the pressure; alternatively, a pressure transducer may be used which can be connected to a data processing unit such as a computer and the pressure data thus aquired may be used to provide the requisite feedback information for specific applications.

In a further embodiment, the unit according to the invention may be provided with a connector adapted to engage the outlet of a nebuliser so as to provide a fluid connection between the outlet of the nebuliser and the mouthpiece for insertion in the subject's mouth, the connector being positioned between the pressure sensing device and the means for providing resistance to the airflow.

The device according to the invention is provided with a controllable variable resistance device which provides a means for controllably varying the airflow resistance provided during inspiration or expiration.

Resistance to airflow may suitably be provided by any means arranged to provide resistance to airflow within the device which may be varied controllably as the user breathes through the device. Any means of restricting the cross-section of the airflow pathway through the device may be used provided that this restriction may be controllably varied during inspiration and/or expiration.

Preferably the resistance is provided by incorporating within the unit of the device according to the invention a diaphragm comprising an orifice through which the air must flow, the dimensions of the orifice being controllable to provide variable resistance to inspiratory or expiratory airflow through the device. It will be appreciated that the diameter of the orifice through which the air must flow will be chosen such that the resistance provided is appropriate for the intended application, the maximum diameter of the orifice being governed by cross-section of the unit within which the diaphragm is incorporated. The orifice will preferably be adjusted to accurately open at 0.1 mm intervals to achieve the requirements and interaction with the algorithmic assessments of lung volume/flow/time and pressure.

Particularly preferably, the diaphragm comprises a variable iris, the diameter of the orifice defined by the iris being controllable, either manually or automatically (for example under the control of a computer) to control the resistance to airflow. The use of a variable iris in a device according to the invention is particularly advantageous as fine adjustments can instantaneously give rise to an almost infinite range of orifice diameters, allowing rapid but controlled variation in resistance to either inspiratory or expiratory airflow and thereby expanding the range of applications to which the device according to the invention can be put.

In a particularly preferred embodiment according to the invention, the unit is provided with means for acquiring and displaying or recording data as the subject breathes in or out, regarding the airflow, the air pressure and the duration of inspiration or expiration. The parameters are preferably recorded in real time and visualised on a screen to provide biofeedback to the user. Typically a data processing unit such as a computer may be used. The acquired data can be used to provide immediate and instantaneous feedback to the user about his actual breathing patterns in relation to targets or to calculate how best to vary the applied resistance to airflow during the breathing cycle. This allows the unit to be used with particular efficacy in its various applications. In pulmonary drug administration, for example, an algorithm can be applied to calculate the exact point in the breathing cycle at which the resistance should be released in order to achieve targeted particle deposition at the desired position in the respiratory tract. Similarly, the pattern of variation of resistance which is optimal to assist the user in effective airway clearance can be computed. Using displayed feedback data the user can also compare his actual breathing profile with an optimised target for the particular application. In respiratory muscle training, the subject can then endeavour to adjust his or her performance in an effort to exceed the target.

Preferably a user of the device will be provided with feedback data whenever he uses it, to ensure that the prescribed breathing profile is maintained and to monitor progress. Alternatively a subject can, after initial training in optimal use of the device with the aid of the feedback data, use the device in a stand-alone fashion, that is without it being connected to the data processing unit. In this way, it would be possible to provide training at a centre such as a hospital but then allow a user to take the device with him wherever he may go, without the need for the ancillary computer equipment. If necessary, the user could then return to the centre for monitoring and further training at appropriate intervals.

The device according to the invention may be used in a variety of applications, particularly in methods for providing improved targeted pulmonary drug deposition, for augmenting airway clearance techniques and in methods for training the respiratory muscles.

For use in targeted deposition of inhaled drugs, the device according to the invention, connected at one end to a suitable mouthpiece attachment and at the other to a pressure sensing device for measuring the pressure achieved, is suitably connected to a nebuliser as described above. The nebuliser may provide a constant flow of inhaled drug or may alternatively provide metered dose inhalation, that is intermittent flow only during inhalation. The nebuliser timing may be integrated with inspiratory times selected from the software or using a timer (for the stand-alone unit) to improve the efficient use of the inhaled drug. Manipulation of the airflow through the device during inspiration or expiration by reducing the resistance causes the pressure to drop and as the equal pressure point nears and full lung volume (total lung capacity) is reached any drugs in suspension within the airway will lose forward momentum and drop towards the lung pulmonary surface. The point at which this occurs will be assessed in the laboratory setting by measuring flow in relation to pressure through a series of selected orifice leaks. When calculated against vital capacity and inspiratory time a working algorithm will be arrived at for any leak/resistance in each individual using the system. Software representations of pressure/time profiles and lung deposition of inhaled drugs may be used to provide real time bio-feedback to users. By means of the invention therefore, different areas of the lungs may be specifically targeted for maximal deposition by manipulation of pressure, flow and time variables using individualised optimal inspiratory efforts based on derived algorithms.

Training of respiratory muscles using the device according to the invention may conveniently be effected using computerised bio-feedback throughout a full lung volume range using the variable leak to obtain the different velocities of muscle shortening which equate to power (high velocity, low resistance) or strength endurance response (high repetition moderate load, high resistance). Using the incremental loading of the TIRE, muscles can be trained until the onset of fatigue. A pyramid of efforts (reversing work rest ratios from hard to easy) will then allow a cool down period. Alternating approaches would allow cross training (mixing strength, power and endurance training on different days) depending upon need. All efforts would be visible in real time on the computer screen at a selected load. At failure to match on screen targets, training would stop (fatigue being reached) and data stored to computer data base. Rest periods and sub-maximal loads based on the best sustained maximal inspiratory pressure (SMIP) will be chosen by medical professionals in order to obtain the desired training effect. Values of work will be expressed in SI units calculated from the algorithms of flow orifice and pressure time relationships. For subjects training there would be the possibility of continued use of the fully integrated system, or alternatively the use of the stand alone unit only but with regular re-assessment upon the master system. If the leak is adjusted between known orifice sizes during a breath, specific training will occur for different fibre types providing a novel training load for the inspiratory muscles.

By using a device according to the invention to vary the resistance to airflow during both inspiration and expiration, known airway clearance techniques may be implemented much more effectively than has hitherto been possible. Varying the resistance during inspiration allows penetration of flow to variable lung volume and varying the resistance during expiration provides back pressure (or positive expiratory pressure, PEP) to prevent premature airways collapse. As described above, the pressure achieved may be measured by incorporating a pressure sensing device such as a manometer or a pressure transducer. This pressure sensing device may be connected to a data processing device such as a computer to provide feedback of pressure/time profiles. Additional software biofeed-back may suitably be provided using a computer model of the lung to integrate pressure, flow and volume parameters. The user may select a particular airway clearance technique from a software menu including accepted descriptions of the technique and use the lung model to accurately breathe to different lung volumes to maximal effect for that individual.

It will be appreciated that one or more of the above methods may be combined. For example, it may be desirable to deliver a drug that affects mucous expectoration to the location of the sputum by firstly targeting delivery of the drug to low lung volume, followed by targeting to mid and high lung volumes as the secretions move towards the mouth prior to expectoration. It may also be desirable to combine targeted delivery of a drug such as a bronchodilator with airway clearance using a method as described above.

The invention may be further illustrated by way of example only by reference to the following figures in which:—

Figure 1:
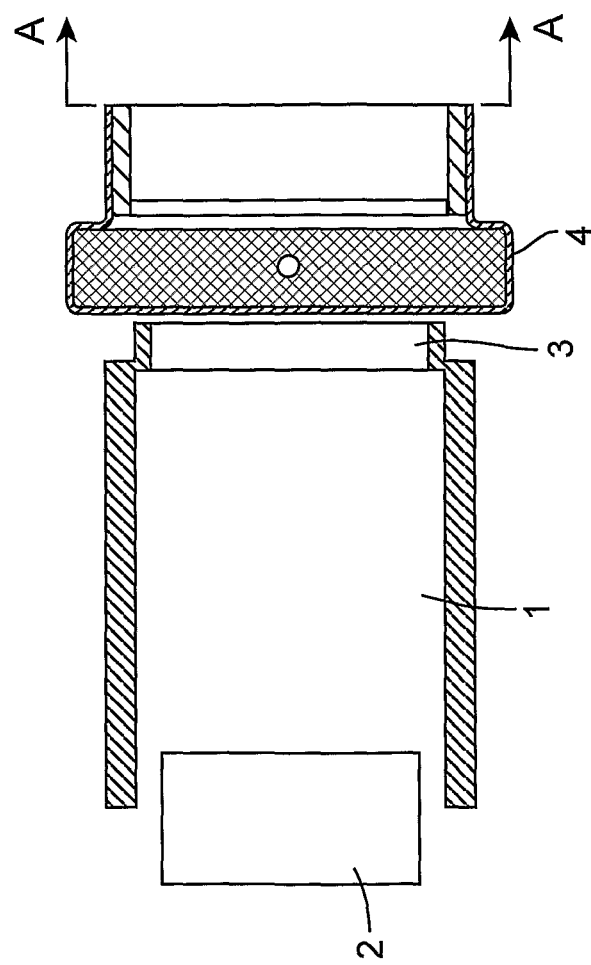
FIG. 1 shows a partial cross-section of a device according to the invention.

Referring to FIG. 1, there is shown a device for use according to the invention comprising a unit (1) having a mouthpiece (2) through which the subject breathes and an air filter (3). Positioned within the unit is a diaphragm (4) having an orifice (typically having a size of 0.1 mm to 12 mm) through which the air must flow, the diaphragm comprising a variable iris which provides variable resistance to airflow during breathing when the iris aperture is opened. The diameter of the diaphragm orifice is controllable manually by means of a lever (not shown) and the device may be calibrated so that the user can readily adjust the size of the orifice to the desired aperture during the respiratory cycle. Alternatively, the diameter of the orifice may be adjusted during the inspiratory or expiratory efforts under the control of a computer.

Figure 2:
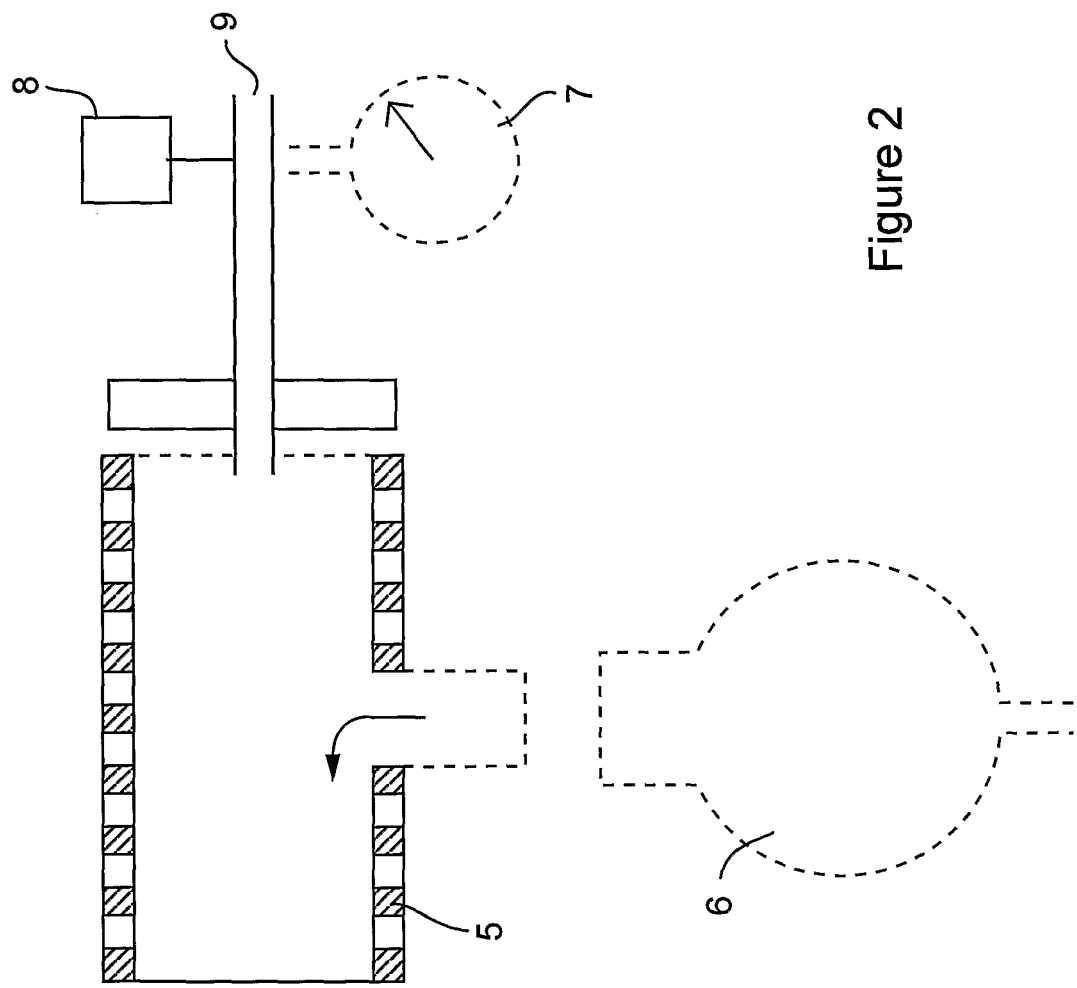
FIG. 2 shows schematically the connections to a nebuliser and pressure monitoring equipment for use with the device of FIG. 1.

FIG. 2 shows how the device of FIG. 1 may be extended (beyond line AA shown in FIG. 1) to incorporate connections for a T-piece nebuliser connector (5) and nebuliser unit (6) and also a pressure sensing device to measure expiratory pressure (PEP). The pressure sensing device may suitably be a simple aneroid manometer (7) in the case of a stand-alone unit or alternatively it may comprise a pressure transducer (8) linked to a computer. Beyond the expiratory pressure tap, the part of the device distal to the mouthpiece (9) through which the exhaled gases escape may be reversibly sealed by a flap valve (not shown) allowing inspiratory airflow but closing to allow measurement of PEP. Oxygen may, if desired, be entrained into the system at this point.

To enable inspiratory measures of pressure, the pressure sensing device is instead situated proximally between the mouthpiece (2) and the diaphragm (4) in the unit shown in FIG. 1.

Figure 3:
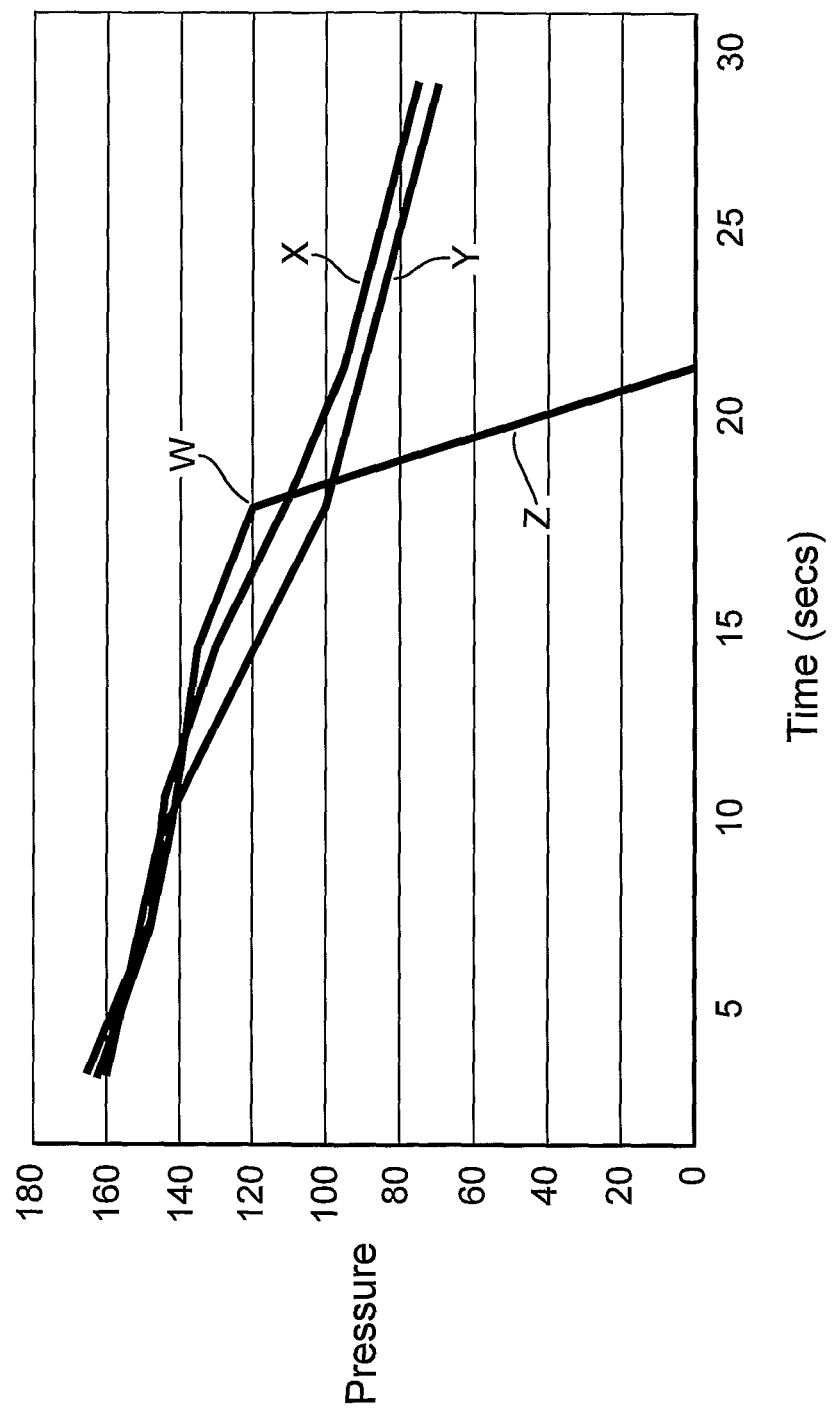
FIG. 3 shows a typical display of the variation of pressure during inspiration in an application of a device according to the invention.

FIG. 3 shows the pressure-time profiles derived from the same subject during inspiration using a device according to FIG. 1 having a pressure tap situated between the mouthpiece and the diaphragm. Lines X and Y were obtained with the subject breathing in maximally through a full volume range with the iris orifice set at 2 mm diameter to provide a small resistance. Line Z was obtained initially under the same conditions but with the iris being fully opened at time point W so that the resistance to the air flow reduces. The resulting rapid drop in negative pressure causes the airflow through the device to reduce.

Figure 4:
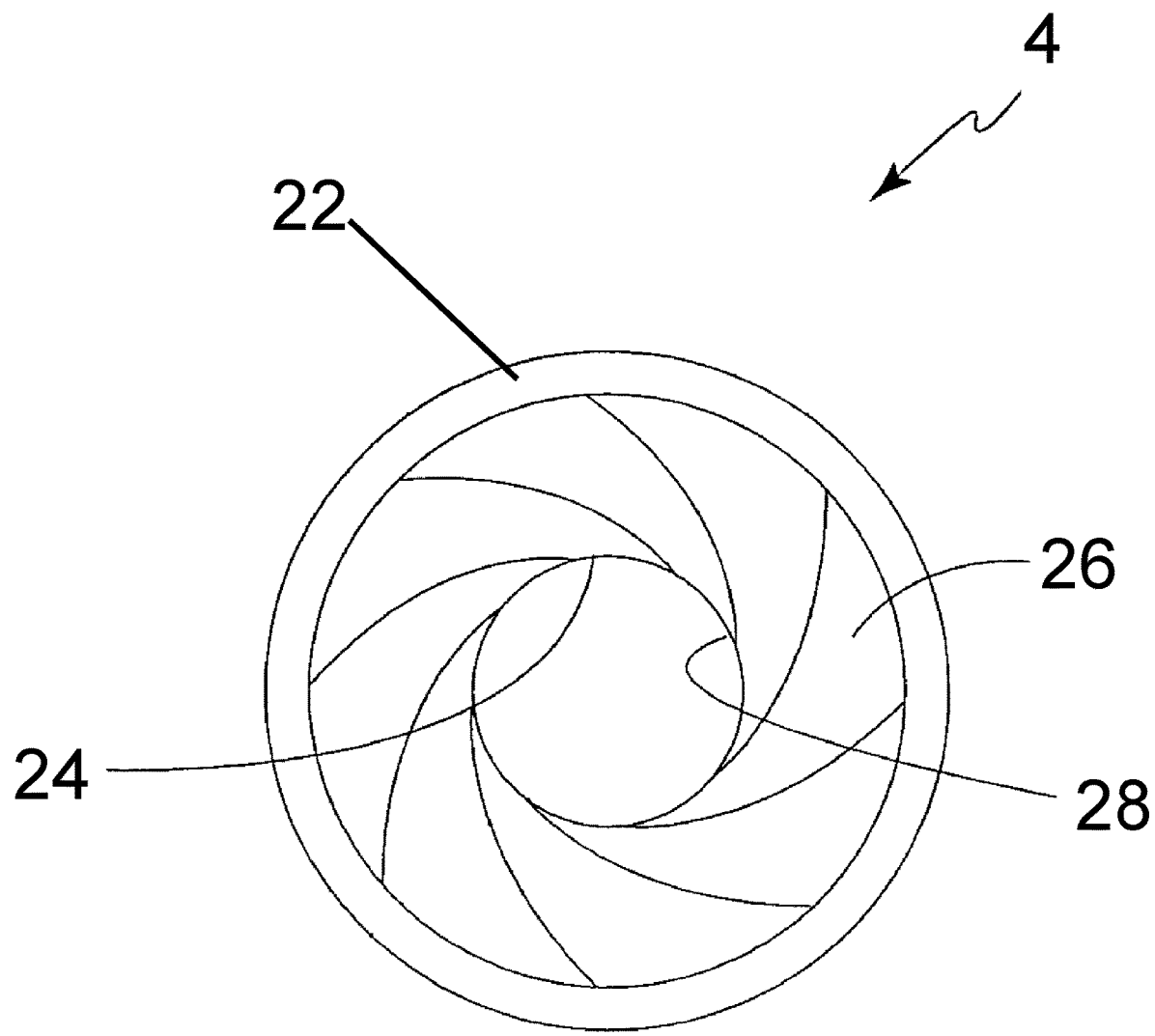
FIG. 4 shows a cross-section of a diaphragm 4 as shown FIG. 1.

FIG. 4 shows a cross-section of one possible embodiment of the diaphragm 4 of the present invention. The orifice 28 is formed by the interleaving of a plurality of leaves 26 having an inner curve 24. The leaves 26 are supported by support ring 22 which also serves as a means to open and close the orifice 28 under either manual or computer control.

One of ordinary skill in the art would well understand that a variable diameter iris would have at least the elements shown in FIG. 4. The embodiment of a diaphragm 4 shown in FIG. 4 is well-known in the prior art.

The invention claimed is:

1. A device comprising:
   a unit through which a subject can breathe,
   the unit comprising an opening to allow airflow communication with the outside of the device,
   a mouthpiece element through which the subject can breathe air in from the device; said mouthpiece element is adapted for insertion into the mouth of a subject and is in fluid communication with the unit;
   a diaphragm having a variable resistance to airflow positioned between the opening and mouthpiece element, such that all airflow passing from outside the device to inside the device, through the mouthpiece element, must pass through the diaphragm and the opening;
   the variable resistance to airflow of the diaphragm being controllable to provide both increasing and decreasing variable resistance during a single inspiratory breath;
   said variable resistance to airflow always allowing some airflow through the unit;
   the unit further comprising a pressure sensing device; and
   a data processor which is in electrical communication with said pressure sensing device and with said diaphragm; said data processor can further perform one or more of the functions selected from the group consisting of acquisition, display and recordation of data from the pressure sensing device, and control of the variable resistance of said diaphragm as the subject breathes in.

2. A device according to claim 1 wherein the unit is provided with a connector adapted to engage an outlet of an aerosol drug delivery device so as to provide a fluid connection between the outlet of the aerosol drug delivery device and the mouthpiece element of the unit.

3. A device according to claim 2 wherein said aerosol drug delivery device is a nebulizer.

4. A device according to claim 2 wherein the variable resistance of the diaphragm can be changed in response to data acquired from the pressure sensing device during a single inspiratory breath.

5. A device according to claim 4 wherein said diaphragm comprises a variable diameter iris.

6. A device according to claim 5 wherein said control of the variable resistance of said diaphragm comprises the ability to increase the diameter of said variable diameter iris during an inspiration so as to cause the reduction of driving pressure at the mouth which causes a decrease in the airflow velocity resulting in a significant decrease in airflow deeper within the lungs which increases inhaled drug deposition at a desired lung volume.

7. A device according to claim 6 wherein said variable diameter iris is electronically controllable and in electrical communication with said data processor and wherein the size of the change in the diameter of the variable diameter iris and when during the inspiration cycle the change occurs is based upon one or more of the parameters selected from the group consisting of airflow, air pressure and duration of inspiration.

8. A device according to claim 6 wherein the variable diameter iris is manually changeable.

9. A device according to claim 7 which is adapted to be able to set the variable diameter to a first diameter and then change the variable diameter orifice to a second larger diameter after a predetermined percentage of the total lung volume of the subject has been drawn in through the device.

10. A device according to claim 7 which is adapted to be able to set the variable diameter orifice to a first diameter and then change the variable diameter orifice to a second larger diameter after a volume of air which is a predetermined percentage of the total lung volume of the subject has been drawn in through the device.

11. A device according to claim 7 in which the device is adapted to be able to set the variable diameter orifice to a first diameter and then change the variable diameter orifice to a second larger diameter after a predetermined period of time has elapsed since the start of the inspiratory breath.

12. A device according to claim 7 wherein the device can be adapted to measure the volume of a full resistive inspiratory breath wherein the variable diameter orifice is set to a known diameter which does not change during the entire the inspiratory breath.

13. A device according to claim 7 wherein the device can be adapted to change the diameter of the variable diameter orifice from a first position to a second position at such time as to cause the deposition of suspended drug delivered within the lung, when an aerosol drug delivery device is connected to the device, at a predetermined volume within the lung based upon a previously measured total lung volume.

14. A device comprising:
a unit through which a subject can breathe,
the unit comprising an opening to allow airflow communication with the outside of the device,
a mouthpiece element adapted for insertion into the mouth of a subject, said mouthpiece element being in fluid communication with the unit and through which the subject can breathe air in from the device;
a diaphragm having a variable diameter orifice positioned between the opening and mouthpiece element, such that all airflow passing from outside the device to inside the device, through the mouthpiece element, must pass through the diaphragm and the opening; the diameter of the orifice always being greater than zero and being electronically controllable to provide both increasing and decreasing variable resistance during a single inspiration;
a connector adapted to engage the outlet of a nebulizer device so as to provide a fluid connection between the outlet of the nebulizer and the mouthpiece element of the unit; and
the diaphragm further being adapted to maintain a fixed orifice diameter during an initial phase of the inspiratory breath and then increase the variable diameter orifice during the remainder of the inspiratory breath so as to cause the reduction of driving pressure at the mouth which causes a decrease in the airflow velocity resulting in a significant decrease in airflow deeper within the lungs which facilitates inhaled drug deposition at a desired lung volume when the connector is attached to a nebulizer.

15. A device according to claim 14 wherein the unit comprises a tubular passageway within which the diaphragm is positioned.

16. A device according to claim 14 wherein the variable diameter orifice comprises a variable diameter iris.

17. A device according to claim 14 wherein the unit further comprises an air filter.

18. A device according to claim 14 wherein the unit is provided with a pressure sensing device.

19. A device according to claim 18 wherein the pressure sensing device is connected to the unit between the mouthpiece element and the diaphragm.

20. A device according to claim 19 wherein the unit further comprises a data processor which can perform one or more of the functions of acquisition, display and recordation of data as the subject breathes in.

21. A device according to claim 20 wherein the data processor is in electrical communication with the pressure sensor and is adapted to acquire from the pressure sensor data on one or more parameters selected from the group consisting of airflow, air pressure, and duration of inspiration.

22. A device according to claim 21 wherein said variable diameter orifice is in electrical communication with and controllable by said data processor; and wherein the size of the change in the diameter of the variable diameter orifice and when during the inspiration cycle the change occurs is based upon one or more of the parameters selected from the group consisting of airflow, air pressure and duration of inspiration.

23. A device according to claim 14 wherein said variable diameter orifice is manually controllable.

* * * * *